United States Patent [19]

Ubel, III et al.

[11] Patent Number: 5,040,976

[45] Date of Patent: Aug. 20, 1991

[54] EXPANDABLE DENTAL IMPRESSION TRAY

[75] Inventors: F. Andrew Ubel, III, St. Paul; Joel D. Oxman, Minneapolis, both of Minn.

[73] Assignee: Minnesota Mining and Manufacturing Company, St. Paul, Minn.

[21] Appl. No.: 484,691

[22] Filed: Feb. 23, 1990

[51] Int. Cl.⁵ ............................................. A61C 9/00
[52] U.S. Cl. ........................................... 433/41; 433/37
[58] Field of Search .................... 433/37, 38, 41, 48; 128/831

[56] References Cited

U.S. PATENT DOCUMENTS

| | | | |
|---|---|---|---|
| 1,561,052 | 11/1925 | Brown | 433/36 |
| 1,955,709 | 4/1934 | Kinsley | 433/48 |
| 3,250,004 | 5/1966 | Jones | 433/48 |
| 3,473,225 | 10/1969 | Deuschle et al. | 433/48 |
| 3,654,703 | 4/1972 | McAdoo | 433/48 |
| 3,878,610 | 4/1975 | Coscina | 433/37 |
| 3,890,711 | 6/1975 | Burns | 433/41 |
| 4,227,877 | 10/1980 | Tureaud et al. | 433/37 |
| 4,361,528 | 11/1982 | Ginsburg et al. | 264/28 |
| 4,401,616 | 8/1983 | Wagner | 264/138 |
| 4,413,979 | 11/1983 | Ginsburg et al. | 433/41 |
| 4,619,610 | 10/1986 | Pelerin | 433/41 |
| 4,684,343 | 8/1987 | Schreinemakers | 433/214 |
| 4,768,951 | 9/1988 | Abiru et al. | 433/48 |

FOREIGN PATENT DOCUMENTS

| | | | |
|---|---|---|---|
| 885772 | 1/1954 | Fed. Rep. of Germany . | |
| 3615821 | 11/1987 | Fed. Rep. of Germany | 433/41 |
| 2606271 | 5/1988 | France | 433/41 |

*Primary Examiner*—Gene Mancene
*Assistant Examiner*—Michael Lynch
*Attorney, Agent, or Firm*—Gary L. Griswold; Walter N. Kirn; James D. Christoff

[57] ABSTRACT

A dental impression tray is made of thermoplastic material which may be heated in order to shape the tray to accommodate the patient's dental arch. The tray includes a channel for receiving impression material, and the channel has a folded section which may be unfolded when the tray is heated in order to increase the height, width or length of the channel. The folded section extends outwardly from the channel and provides convenient gripping structure for removing the tray from the mouth after the impression is taken.

10 Claims, 1 Drawing Sheet

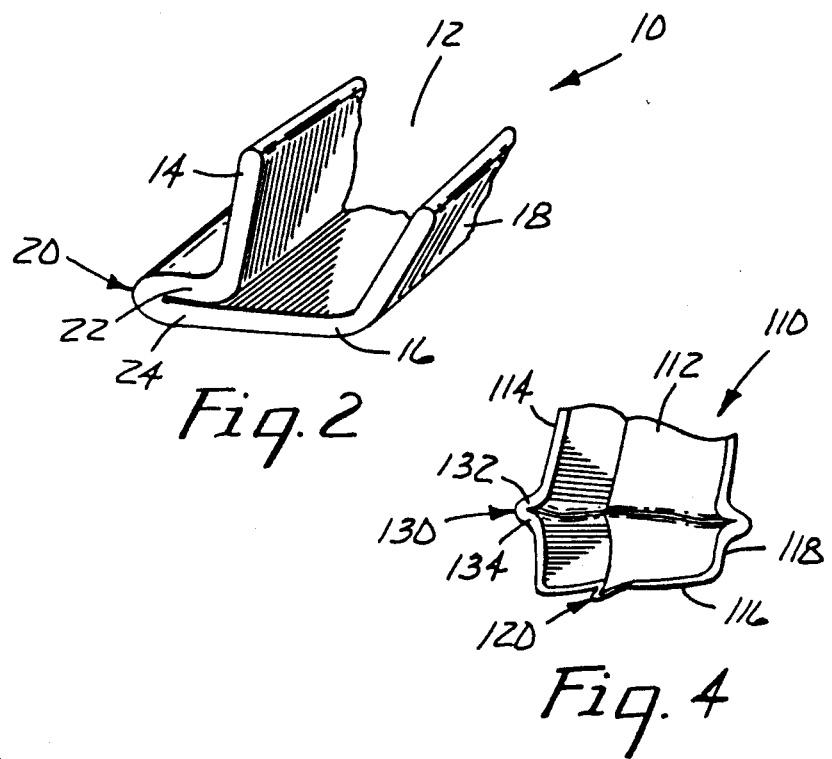
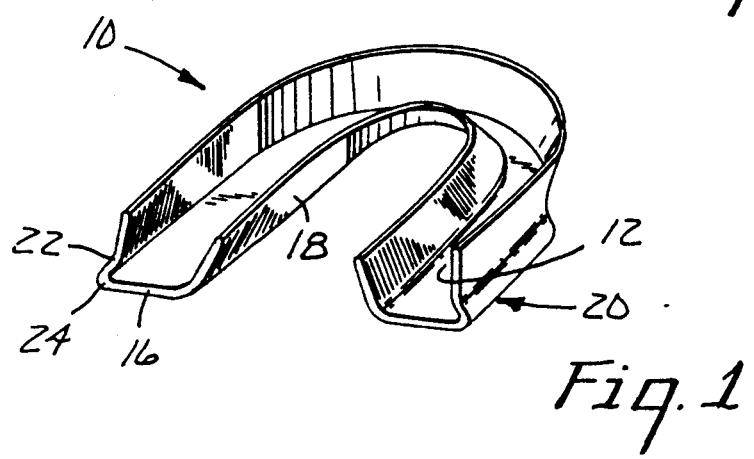
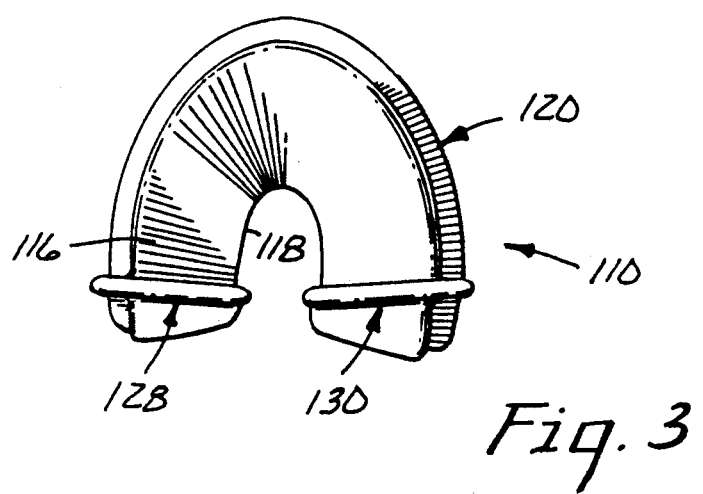

EXPANDABLE DENTAL IMPRESSION TRAY

BACKGROUND OF THE INVENTION

1. Field of the Invention

This invention relates to a thermoplastic dental impression tray that may be shaped to conform to a patient's dental arch.

2. Description of the Related Art

Dental impression trays are used to hold impression material for making a model of a patient's oral cavity so that a crown, bridge, denture, restoration or the like can be made. To make the model, a quantity of impression material is placed in an open trough or channel of the tray, and the tray is then pressed onto the dental arch to make a female cast of the desired area of interest. The cured impression is then used to form a male model which replicates the selected area of the patient's arch.

Recently, there has been increased interest in the use of thermoplastic impression trays which may be heated and then shaped to closely conform to the patient's dental anatomy. Since dimensions of the dental arch may vary widely from patient to patient, such trays may be molded when heated to adjust the height and width of the channel of the tray to accommodate the selected area of the patient's. arch In this manner, the tray may be shaped to conform to the arch so that an accurate impression may be made, while enabling the relatively expensive impression material to fully surround the selected area of the arch without wastage. Examples of such moldable impression trays are described in U.S. Pat. Nos. 4,227,877, 4,361,528 and 4,657,509.

The height and width of the channel of known moldable impression trays may be expanded only to certain practical limits. For example, if the height of the channel is enlarged beyond a certain dimension as the tray is molded, the width of the channel may decrease to a dimension too small to accommodate the width of the arch. On the other hand, decreasing the height of the channel when molding the tray may increase the width of the channel to a dimension much greater than needed, such that a certain amount of the impression material is wasted. Another problem is encountered when the patient's arch is longer than average and cannot be accommodated by the tray at hand.

The aforementioned U.S. Pat. No. 4,227,877 illustrates a moldable maxillary impression tray having a U-shaped trough that is connected to a central section for engaging the vault of the patient's palate. The vault engaging section includes a central pleat extending in the sagittal plane, and the pleat allows lateral adjustment of the distance between the two posterior end portions of the trough when the tray is heated, so that central vault section of the tray may be adjusted to compensate for the concavity of the palatal region of the individual patient. However, such construction does not satisfactorily overcome the problem of readily conforming the height, width or length of the trough to accommodate the configuration of the patient's dental arch.

SUMMARY OF THE INVENTION

The present invention is directed toward a dental impression tray having an elongated channel adapted to receive a quantity of impression material. The tray is comprised of a thermoplastic material that is malleable at elevated temperatures. The channel includes a buccal side, an occlusal side and a lingual side adapted to extend about buccal, occlusal and lingual regions respectively of at least a portion of a dental arch. Advantageously, the channel includes an outwardly extending folded section, whereby the size of the channel may be enlarged by partial unfolding of the folded section when the tray is heated to elevated temperatures.

The folded section, being adjacent the channel, provides structure which may be firmly engaged by the dentist's fingers when removing the tray from the mouth. As a result, the tray may be carefully grasped and pulled from the teeth and surrounding tissue in a direction parallel to the sagittal plane without excessive tipping or rotation of the tray, so that the resulting impression is not unduly distorted.

BRIEF DESCRIPTION OF THE DRAWINGS

FIG. 1 is a top, rear and left side perspective view of a dental impression tray constructed in accordance with the present invention;

FIG. 2 is an enlarged top, rear and left side perspective view in fragmentary form of the right rear end portion of the tray shown in FIG. 1, except that a section of a channel of the tray is illustrated in a more tightly folded configuration;

FIG. 3 is a bottom view of a dental impression tray in accordance with another embodiment of the invention; and right rear portion of the tray shown in FIG. 3

DETAILED DESCRIPTION OF THE PREFERRED EMBODIMENT

A dental impression tray in accordance with a preferred embodiment of the invention is broadly designated by the numeral 10 in FIGS. 1 and 2. The tray 10 is made from a single sheet of thermoplastic material and has an overall, generally U-shaped configuration in plan view.

Preferred thermoplastic molding compositions for making the tray 10 are described in our copending U.S. patent applications Ser. Nos. 484,695 and 484,692 the disclosures of which are incorporated in this specification by reference. Such compositions comprise a blend which includes polycaprolactone, and are characterized as being solid at 38° C., and having a melting or softening point that can comfortably be withstood by oral tissues The heated tray 10 may thus be shaped while in the oral cavity or, if desired, while outside of the oral cavity The tray 10 includes an elongated, continuous channel 12 having an open top. The channel 12 includes a buccal side 14, an occlusal side 16 and a lingual side 18 adapted to extend about buccal, occlusal and lingual regions respectively of a dental arch. As used herein, "dental arch" means the dentulous or edentulous maxillary or mandibular alveolar ridge (i.e., the bony ridge of either jaw and the surrounding mucosae along with any associated teeth), and does not include the palatal area of the oral cavity.

The channel 12 includes a folded section 20 having a gingival portion 22 that is integrally connected to the occlusal-most end of the buccal side 14, and an occlusal portion 24 that is integrally coupled to a buccal-most end of the occlusal side 16. As shown in FIG. 2, the tray 10 may be shipped to the dentist in a configuration such that the gingival portion 22 extends essentially parallel to the occlusal portion 24 and is in flat, face-to-face contact with the latter. In this configuration, the buccal side 14 extends at an angle of about 90 degrees relative to the gingival portion 22, and the occlusal side 16 is coplanar with the occlusal portion 24. The lingual side 18 curves upwardly and outwardly away from the occlusal side 16 and has an outer straight section which lies at an angle of about 120 degrees relative to the occlusal side 16.

Once the tray 10 is heated to its softening temperature, the tray 10 is pliable and may be molded by hand to closely conform to the dental arch. If, for example, a relatively wide channel is needed to accommodate the arch, the tray 10 when softened may be formed so that the folded section 20 is partially unfolded and moves from the orientation shown in FIG. 2 to the orientation shown in FIG. 1 that directly faces the area or ridge. The movement of the gingival portion 22 away from the occlusal portion 24 enables the previously gathered portion of the channel 12, namely the folded section 20, to be molded along with the sides 14, 16 and 18 to permit the occlusal dimension or height of the channel 12 to be enlarged as necessary. In practice, either or both of the sides 14, 18 may be extended in height by proper hand-forming of the softened channel 12, in addition to enlarging the height of the channel, or as an alternative to the latter, it is also possible to enlarge the buccal-lingual width of the channel 12 once the folded section 20 is unfolded or partially unfolded.

Advantageously, the folded section 20 extends along the entire lower perimeter of the channel 12 including anterior as well as both posterior portions of the tray 10. As such, the folded section 20, whether in the configuration shown in FIG. 1 or FIG. 2, provides convenient structure for gripping the tray 10 after the impression of the patient's arch has been taken. The outwardly extending folded section 20 enables the dentist's fingers to grasp both sides of the tray 10 and firmly pull the tray 10 away from the patient's arch. The tray 10 can thus be readily removed without undue tilting or rotation of the tray which might otherwise cause unsatisfactory distortion in the resultant impression.

Further, the peripheral folded section 20 obviates the need for the relatively long anterior handle frequently found in dental impression trays. The use of such anterior handles increases the likelihood that the tray will be unduly pivoted or tilted as the tray is removed from the mouth which, in turn, raises the probability that the resultant impression may be unduly distorted. Moreover, such handles hinder shaping of the malleable material in the anterior region of the channel where the handle is connected to the channel.

An alternate embodiment of the invention is shown in FIGS. 3 and 4 and includes a tray 110 having a channel 112 generally similar to the channel 12 of the tray 10 shown in FIGS. 1 and 2. The channel 112 thus has a buccal side 114, an occlusal side 116 and a lingual side 118, and a gathered or folded section 120 which extends around substantially the entire lower, exterior extent of the tray 110.

The tray 110, however, includes two additional folded sections 128, 130 which are located in opposed posterior portions of the tray 110 and which extend in a direction transverse to the longitudinal axis of the folded section 120. With reference to FIG. 4, the transverse folded section 130 includes a mesial portion 132 and a distal portion 134, both of which are integrally connected with the channel 112 and extend along the entire extent of the buccal side 114, the occlusal side 116 and the lingual side 118. When the tray 110 is in the configuration shown in FIGS. 3 and 4, the mesial portion 132 abuts the distal portion 134 in essentially parallel, flat, face-to-face contact with the same. Likewise, the transverse folded section 128 has mesial and distal portions similar to the portions 132, 134 of the folded section 130.

In instances where the patient has an arch longer in length than the length of the channel 112, the posterior portions of the tray 110 may be elongated by warming the latter to its softening temperature, and then unfolding the folded sections 128, 130 by pulling the posterior ends of the tray 110 away from the anterior portion of the same. The portions 132, 134 may be moved as much or as little as needed to expand the length of the channel 112 in order to thereby accommodate the length of the patient's arch. If desired, the folded section 120 may also be unfolded or partially unfolded, so that the height or width of the channel 112 may also be shaped to accommodate the patient's arch. The folded sections 128, 130, along with the folded section 120, provide convenient structure for handling the tray in stable fashion.

We claim:

1. A dental impression tray having an elongated impression channel adapted to receive a quantity of impression material, said tray comprised of a thermoplastic material malleable at elevated temperatures, said channel including a buccal side, a lingual side facing said buccal side and an occlusal side between said lingual side and said buccal side, said buccal side, said lingual side and said occlusal side adapted to extend about buccal, occlusal and lingual regions respectively of at least a portion of an alveolar ridge, at lest one of said lingual side, said buccal side and said occlusal side including an outwardly extending folded section that may be partially unfolded when said channel is heated to elevated temperatures to an orientation directly facing the alveolar ridge in order to enlarge the size of said impression channel and extend said channel further about the alveolar ridge.

2. The tray according to claim 1, wherein said folded section extends in an occlusal plane substantially parallel to said occlusal side.

3. The tray according to claim 2, wherein said folded section is directly connected to said buccal side of said channel.

4. The tray according to claim 3, wherein said folded section includes an occlusal portion substantially coplanar with said occlusal side of said channel.

5. The tray according to claim 1, wherein said folded section extends substantially the entire length of said channel.

6. The tray according to claim 1, wherein said tray is generally U-shaped in plan view, and wherein said folded section extends substantially along the entire perimeter of said channel.

7. The tray according to claim 1, wherein said folded section extends in a direction substantially perpendicular to the longitudinal axis of said channel.

8. The tray according to claim 7, wherein said folded section extends along substantially the entire extent of said buccal side, said occlusal side and said lingual side.

9. The tray according to claim 7, wherein said tray has a posterior portion, and wherein said folded section is located in said posterior portion.

10. The tray according to claim 1, wherein said tray has a substantially U-shaped configuration in plan view, and wherein said folded section extends substantially along the length of said channel; and including a second folded section extending in a direction substantially perpendicular to the longitudinal axis of said channel.

* * * * *

UNITED STATES PATENT AND TRADEMARK OFFICE
CERTIFICATE OF CORRECTION

PATENT NO. : 5,040,976

DATED : August 20, 1991

INVENTOR(S) : F. Andrew Ubel, III and Joel D. Oxman

It is certified that error appears in the above-identified patent and that said Letters Patent is hereby corrected as shown below:

Col. 2, line 27, after "and" insert -- ¶ FIG. 4 is an enlarged, fragmentary, top view of a --.

Col. 2, line 46, after "tissues" insert -- . --.

Col. 2, line 48, after "cavity" insert -- . --.

Col. 3, line 14, delete "area or" and insert -- alveolar --.

Col. 4, line 29, "lest" should be -- least --.

Signed and Sealed this

Sixteenth Day of March, 1993

Attest:

STEPHEN G. KUNIN

*Attesting Officer*     *Acting Commissioner of Patents and Trademarks*